United States Patent [19]

Ebel et al.

[11] Patent Number: 5,354,937
[45] Date of Patent: Oct. 11, 1994

[54] 2-TERT-AMYL COMPOUNDS

[75] Inventors: Klaus Ebel, Ludwigshafen; Juergen Schroeder, Viernheim, both of Fed. Rep. of Germany

[73] Assignee: BASF Aktiengesellschaft, Ludwigshafen, Fed. Rep. of Germany

[21] Appl. No.: 129,333

[22] Filed: Sep. 30, 1993

[30] Foreign Application Priority Data

Oct. 5, 1992 [DE] Fed. Rep. of Germany ....... 4233387

[51] Int. Cl.$^5$ .................... C07C 2/76; C07C 2/78; C07C 5/08
[52] U.S. Cl. .................... 585/601; 568/873; 568/909.5; 552/265
[58] Field of Search ................. 585/601, 609

[56] References Cited

U.S. PATENT DOCUMENTS

| | | |
|---|---|---|
| 4,087,458 | 5/1978 | Emori et al. |
| 4,347,388 | 8/1982 | Gramlich et al. ............ 568/840 |
| 4,895,984 | 1/1990 | Eggersdorfer et al. ....... 568/319 |

FOREIGN PATENT DOCUMENTS

| | | |
|---|---|---|
| 248423 | 6/1987 | European Pat. Off. |
| 2013299 | 3/1970 | Fed. Rep. of Germany. |
| 2460922 | 7/1975 | Fed. Rep. of Germany. |
| 2720294 | 11/1977 | Fed. Rep. of Germany. |
| 946980 | 6/1949 | France. |

OTHER PUBLICATIONS

CA 109(5): 374736, Hoshi et al, Synthesis of 2–tert–alkyl–1,3–butadienes, 1987.
CA 105(19): 171495f Toda et al, Complex of Tertiary acetylenic alcohol and brucine or sparteine, 1985.
Chem. Abstr., vol. 80, (1974) 47 709.

*Primary Examiner*—Johann Richter
*Assistant Examiner*—Rebecca Cook
*Attorney, Agent, or Firm*—Keil & Weinkauf

[57] ABSTRACT

Tert-amyl compounds of the general formula I

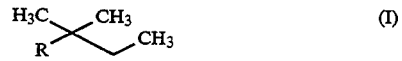

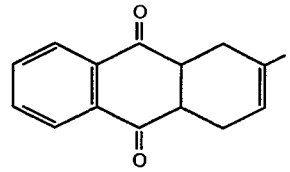

and novel processes for preparing 2-tert-amylbutadiene by dehydrating 3,4,4-trimethylhex-1-en-3-ol at from 100° to 350° C. and from 0.01 to 50 bar on acidic catalysts, its preparation by partially hydrogenating 3,4,4-trimethyl-hex-1-yn-03-ol at from 0° to 50° C. and from 0.01 to 50 bar and its preparation by reacting tert-amyl methyl ketone (3,3-dimethylpentan-2-one) with acetylene in the presence of basic catalysts at from 0° to 60° C. and from 0.01 to 50 bar, and also the preparation of 2-tert-amylanthraquinone by reacting 2-tert-amyl-butadiene with 1,4-naphthoquinone at from 20° to 200° C. and from 0.01 to 50 bar to give 2-tert-amyl-1,4,4a,9a-tetrahydroanthraquinone and then oxidizing the latter in the presence of a strong base at from 0° to 50° C. are described.

1 Claim, No Drawings

2-TERT-AMYL COMPOUNDS

The present invention relates to novel 2-tertamyl compounds, processes for their preparation and the reaction of 2-tert-amylbutadiene to give 2-tert-amylanthraquinone [2-(2-methylbut-2-yl)anthraquinone].

The preparation of 2-tert-amylanthraqiuinone by reacting tert-amylbenzene with a five-fold excess of phthalic anhydride in order to suppress the isomerization of the tert-amyl group is known from Chem. Abstr., Vol. 80, (1974) 47 709 and the subsequent cyclization of the resulting (4-tert-amylbenzoyl)benzoic acid with conc. sulfuric acid has been described.

DE-A-2 720 294 discloses a process for preparing 2-tert-amylanthraquinone by Friedel-Crafts acylation, in which the hydrogen chloride set free has to be stripped off in order to suppress the isomerization of the tertamyl group.

EP-A-248 423 discloses that the isomerization of the tert-amyl group is suppressed in the Friedel-Crafts acylation of phthalic anhydride with tert-amylbenzene if the hydrogen chloride set free is trapped by reaction with an alkylaluminum chloride.

DE-A-2 013 299 describes a process for preparing tert-amylanthraquinone in which (4-tert-amylbenzoyl)-benzoic acid is prepared in a Grignard reaction of phthalic anhydride with 4-tert-amylphenylmagnesium chloride.

The previous processes have the disadvantage that large amounts of salt are produced during the preparation of 2-tert-amylanthraquinone and the isomerization of the tert-amyl group has to be suppressed by additional measures.

It is an object of the present invention to remedy the abovementioned disadvantages.

we have found that this object is achieved by the novel tert-amyl compounds of the general formula I

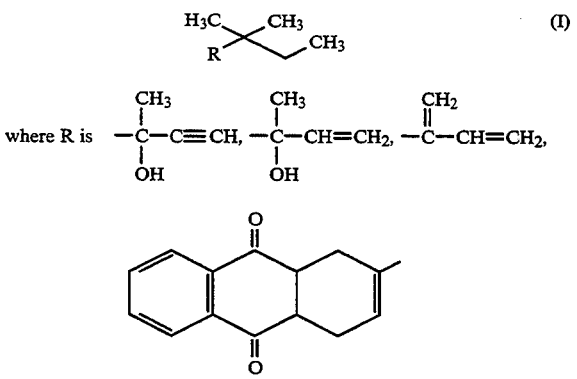

and novel processes for preparing 2-tert-amylbutadiene by dehydrating 3,4,4-trimethylhex-1-en-3-ol at from 100° to 350° C. and from 0.01 to 50 bar on acidic catalysts, its preparation by partially hydrogenating 3,4,4-trimethyl-hex-1-yn-3-ol at from 0° to 50° C. and from 0.01 to 50 bar and its preparation by reacting tert-amyl methyl ketone (3,3-dimethylpentan-2-one) with acetylene in the presence of basic catalysts at from 0° to 60° C. and from 0.01 to 50 bar, and also the preparation of 2-tert-amylanthraquinone by reacting 2-tert-amylbutadiene with 1,4-naphthoquinone at from 20° to 200° C. and from 0.01 to 50 bar to give 2-tert-amyl-1,4,4a,9a-tetrahydroanthraquinone and then oxidizing the latter at from 0° to 50° C. in the presence of a strong base.

The following novel compounds have been found:
2-tert-amylbutadiene
3,4,4-trimethylhex-1-en-3 -ol
3,4,4-trimethylhex-1-yn-3 -ol
2-tert-amyl-1,4,4a, 9a-tetrahydroanthraquinone=2-(2-methylbut-2-yl)-1,4,4a, 9a-tetrahydroanthraquinone The processes according to the invention can be carried out as follows:

Preparation of 2-tert-amylbutadiene 3,4,4-Trimethylhex-1-en-3-ol can be dehydrated at from 100 to 350° C. and from 0.01 to 50 bar in the liquid phase or preferably in the gas phase on acidic catalysts, e.g. also according to Houben-Weyl, Methoden der organischen Chemie (Methods of Organic Chemistry), Volume 5/lb, pages 45 to 104. The resulting 2-tert-amylbutadiene may preferably be continuously removed by distillation and directly processed as a crude product or distilled again.

For the liquid phase procedure suitable temperatures are from 100° to 300° C., preferably 130° to 250° C., particularly preferably 140° to 200° C. As a rule, an inert high-boiling solvent and the acidic catalyst are initially introduced and the 3,4,4-trimethylhex-1-en-3-ol is added dropwise.

Suitable acidic catalysts as a rule are all acidic heterogeneous catalysts, preferably homogeneous catalysts. Acidic homogeneous catalysts which may be mentioned are, for example, mineral acids such as sulfuric and phosphoric acid.

The acidic homogeneous catalysts are employed as a rule in a molar ratio from 0.001:1 to 0.05:1, preferably 0.005:1 to 0.04:1, particularly preferably 0.01:1 to 0.02:1 to the 3,4,4-trimethylhex-1-en-3-ol.

Suitable inert high-boiling solvents are, for example, polyethylene glycol, polypropylene glycol, vacuum gas oil and technical white oil, preferably polyethylene glycol.

Solvents are not necessary as a rule in the gas phase procedure. The reaction temperatures are from 150° to 350° C., preferably 180° to 300° C., particularly preferably 200° to 250° C. The gas mixture leaving the reactor is as a rule condensed. The organic phase can be distilled or directly processed.

Suitable acidic catalysts as a rule are all acidic homogeneous catalysts, preferably heterogeneous catalysts. Acidic heterogeneous catalysts which may be mentioned, for example, are acidic oxides of elements of main groups III and IV and also subgroups IV to VI of the Periodic Table of the Elements, such as silica in the form of silica gel, kieselguhr, quartz, titanium dioxide, zirconium dioxide, phosphorus pentoxide, vanadium pentoxide, boron oxide, aluminum oxide, chromium oxides, molybdenum oxides, tungsten oxides or mixtures thereof, if desired with addition of phosphoric acid, expediently in an amount from 1 to 30% by weight, in particular 5 to 15% by weight, of phosphoric acid, preferably gamma-aluminum oxide.

Preparation of 3,4,4-trimethylhex-1-en-3-ol 3,4,4-Trimethylhex-l-yn-3-ol can be hydrogenated at from 0° to 50° C., preferably 5° to 20° C., and from 0.01 to 50 bar, preferably 0.1 to 10 bar, particularly preferably 0.5 to 5 bar, in a hydrogen atmosphere, in the presence or absence of an inert solvent on partial hydrogenation catalysts, such as e.g. according to Houben-Weyl, Methoden der organischen Chemie (Methods of Organic Chemistry), Volume 4/lc, pages 107 to 109.

After hydrogen absorption is complete, the catalyst is as a rule filtered off and the solvent is removed by distillation. The crude product can be directly processed or distilled again.

Suitable partial hydrogenation catalysts are, for example, Lindlar catalysts which are poisoned, e.g. with quinoline.

The weight ratio of 3,4,4-trimethylhex-1-yn-3-ol to the partial hydrogenation catalyst is as a rule from 1:1 to 1000:1, preferably 10:1 to 500:1, particularly preferably 50:1 to 300:1.

Suitable inert solvents are, for example, $C_4$- to $C_{30}$-alkanes such as butanes, pentanes, hexanes, heptanes, octanes and petroleum ethers, preferably petroleum ethers.

Preparation of 3,4,4-trimethylhex-1-yn-3-ol 2-tert-Amyl methyl ketone can be reacted with acytylene in the presence of basic catalysts at from 0° to 60° C., preferably 10° to 40° C., particularly preferably 15° to 35° C. and from 0.01 to 50 bar, preferably 1 to 30 bar, particularly preferably 5 to 25 bar, in the presence or absence of an inert solvent, e.g. also according to Annalen der Chemie, Volume 596, (. . .) 1 to 224. Working up can be carried out by generally known methods such as e.g. by neutralizing with formic acid, filtering off and if desired distilling the crude product.

Suitable basic catalysts are, for example, alkali metal and alkaline earth metal alkoxides. Suitable alkali metal alkoxides are lithium, sodium, potassium, rubidium and cesium alkoxides, preferably lithium, sodium and potassium alkoxides of any desired alcohols such as $C_1$-to $C_{20}$-alcohols. As a rule, alkali metal alkoxides of $C_1$-to $C_4$-alcohols such as sodium methoxide, sodium ethoxide, potassidm methoxide, potassium ethoxide and potassium tert-butoxide are used, preferably alkali metal alkoxides of $C_1$- and $C_2$-alcohols such as sodium methoxide, sodium ethoxide, potassium methoxide and potassium ethoxide, particularly preferably sodium methoxide.

The molar ratio of basic catalyst (e.g. alkali metal alkoxide) to the tert-amyl methyl ketone is as a rule from 0.001:1 to 1:1, preferably 0.01:1 to 0.5:1, particularly preferably 0.02:1 to 0.2:1.

The basic catalysts such as the alkali metal alkoxides can be employed in the reaction as solids. For process engineering reasons, however, it is advantageous to work with solutions of the catalysts.

In principle all solvents can be used which are stable to the basic catalysts used and under the reaction conditions, such as all customary alcohols such as $C_1$- to $C_{20}$-alcohols, preferably $C_1$- to $C_4$-alcohols such as methanol, ethanol, propanol, isopropanol, butanol, sec-butanol, isobutanol and tert-butanol, particularly preferably methanol and ethanol, acyclic and cyclic ethers such as diethyl ether, methyl tert-butyl ether, tetrahydrofuran and dioxane, preferably tetrahydrofuran.

An alcoholic solution of the alkoxides has proven particularly advantageous, since these solutions can be simply prepared, e.g. by dissolving the respective metals in the alcohol concerned. A solution of sodium methoxide in methanol is particularly preferred.

The amount of solvent can be selected within wide ranges, but it is expediently from 50 to 500 ml, preferably 70 to 200 ml of alcohol per mol of 2-tert-amyl methyl ketone.

2-tert-Amyl methyl ketone can also be reacted with actylene Grignard solutions to give the corresponding propargyl alcohols at from (−20°) to 50° C., preferably (−10°) to 30° C., particularly preferably 0° to 20° C. and from 0.01 to 50 bar, preferably 0.1 to 5 bar, particularly preferably at atmospheric pressure, in the presence or absence of an inert solvent, e.g. analogously to Preparative Acetylenic Chemistry, 2nd Edition, Verlag ELSEVIER.

Suitable inert solvents are, for example, acyclic and cyclic ethers such as diethyl ether, methyl tertbutyl ether, tetrahydrofuran and dioxane, preferably tetrahydrofuran.

The molar ratio of the acetylene Grignard compound to tert-amyl methyl ketone is as a rule from 0.7:1 to 3:1, preferably 0.9:1 to 2:1, particularly preferably 1:1 to 1.5:1. The hydrolysis can be carried out according to generally known conditions, e.g. using 2N hydrochloric acid, subsequent separation of the organic phase and if desired distillation of the product.

Reaction of 2-tert-amylbutadiene 2-tert-Amyl methyl ketone and 1,4-naphthoquinone can be reacted to give 2-tert-amyl-1,4,4a,9a-tetrahydroanthraquinone by Dieis-Alder reaction at from 20° to 200° C., preferably 50° to 120° C. and from 0.01 to 50 bar, preferably 0.1 to 5 bar, particularly preferably atmospheric pressure, in the presence of an inert solvent, and then, if desired after distillative return of unreacted 2-tert-amylbutadiene, oxidized with air at from 0° to 50° C. preferably 15° to 40° C. in the presence of a strong base, e.g. analogously to Org. Synth., Coll. Vol. III, (1955) 310 to 311.

The molar ratio of 1,4-naphthoquinone to the 2-tert-amylbutadiene is in general from 0.2:1 to 5:1, preferably 0.5:1 to 2:1, particularly preferably 1:1 to 1.5:1.

Suitable inert solvents are, for example, $C_1$- to $C_{20}$-alcohols, preferably $C_1$- to $C_4$-alcohols such as methanol, ethanol, propanol, isopropanol, butanol, sec-butanol, isobutanol and tert-butanol.

Suitable strong bases, are, for example, hydroxides such as lithium hydroxide, sodium hydroxide and potassium hydroxide, preferably potassium hydroxide.

The compounds according to the invention 2-tert-amylbutadiene, 3,4,4-trimethylhex-1-en-3-ol, 3,4,4-trimethylhex-1-yn-3-ol and 2-tert-amyl-1,4,4a,9a-tetrahydroanthraquinone [2-(2-methylbut-2-yl)-1,4,4a,-9atetrahydroanthraquinone] are suitable for preparing 2-tert-amylanthraquinone. The latter is employed as a catalyst for $H_2O_2$ synthesis (Ullmanns Encyclopädie der technischen Chemie (Ullmann's Encyclopedia of Industrial Chemistry), 4th Edition, Volume 17, pages 694 to 711).

EXAMPLES

Preparation of 3,4,4-Trimethylhex-1-yn-3-ol

Example 1

32 g of tert-amyl methyl ketone and 15 g of sodium methoxide were suspended in 50 ml of tetrahydrofuran in an autoclave and pressurized with acetylene at room temperature with stirring up to a constant pressure of 20 bar. After reaction was complete, the pressure was released, the mixture was neutralized with formic acid and filtered, and the solvent was removed by distillation. The conversion was 66% with a selectivity of 90%.

Example 2

50 g of tert-amyl methyl ketone were dissolved in 50 ml of tetrahydrofuran and the solution was added dropwise at 0° C. to 330 ml of a 1.5 molar acetylene Grignard solution in tetrahydrofuran. After 30 min, the mixture was hydrolyzed with 2N hydrochloric acid, the organic phase was separated, the solvent was removed and the residue was then fractionally distilled. 52 g (85%) of 3,4,4-trimethylhex-1-yn-3-ol were obtained (b.p.: 110° C./175 mbar).

Preparation of 3,4,4-Trimethylhex-1-en-3-ol

Example 3

100 g of 3,4,4-trimethylhex-1-yn-3-ol, 3 g of quinoline and 5.4 g of Lindlar catalyst were initially introduced in 100 ml of petroleum ether and the mixture was stirred at 25° C. for 10 hours under a hydrogen atmosphere. The catalyst was then filtered off, the filtrate was concentrated and the residue was analyzed by means of GC. 91 g (90%) of 3,4,4-trimethylhex-1-en-3-ol were obtained. The residue was processed without purification.

A part of the product was distilled to characterize it. The boiling point was 78° C. at 30 mbar.

Preparation of 2-Tert-Amylbutadiene

Example 4

40 g of 3,4,4-trimethylhex-1-en-3-ol were added dropwise to a mixture of 200 g of polyethylene glycol and 3 g of phosphoric acid at from 285° C. to 290° C. in the course of 2 hours. The organic phase of the two-phase mixture discharged was analyzed by means of GC. 24 g (70%) of 2-tert-amylbutadiene were obtained. The organic phase was processed without purification.

Example 5

25 g of 3,4,4-trimethylhex-1-en-3-ol hourly were evaporated by means of an evaporator and passed over 100 ml of a gamma-aluminum oxide catalyst at 220° C. The reaction gases were then cooled and collected in a receiver. The phases were then separated and the organic phase was analyzed by means of GC. 35 g (80%) of 2-tert-amylbutadiene were obtained.

A part of the product was distilled to characterize it. The boiling point was from 115° to 120° C. at 700 mbar.

Preparation of 2-Tert-Amylanthraquinone

Example 6

20 g of 2-tert-amylbutadiene, 25 g of 1,4-naphthoquinone and 300 ml of butanol were heated at 70° C. for 8 hours. The mixture was then treated with 30 g of potassium hydroxide and air was introduced at from 25° C. to 33° C. for 8 hours. After removing the solvent and recrystallizing from cyclohexane, 35 g (80%) of 2-tertamylanthraquinone of melting point from 75° to 76° C. were obtained.

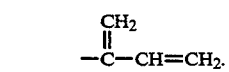

We claim:

1. A tert-amyl compound of formula I

   (I)

where R is